(12) United States Patent
Scharlf-Afschar et al.

(10) Patent No.: US 6,878,534 B1
(45) Date of Patent: Apr. 12, 2005

(54) CONTINUOUS FERMENTATION PROCESS WHICH IS USEFUL FOR THE SIMULTANEOUS OPTIMAL PRODUCTION OF PROPIONIC ACID AND VITAMIN $B_{12}$

(75) Inventors: Abbas Scharlf-Afschar, Braunschweig (DE); Adolfo Quesada-Chanto, Wolfenbüttel (DE)

(73) Assignee: Gesellschaft fur Biotechnologische, Braunschweig (DE)

( * ) Notice: Subject to any disclaimer, the term of this patent is extended or adjusted under 35 U.S.C. 154(b) by 0 days.

(21) Appl. No.: 08/603,179

(22) Filed: Feb. 20, 1996

Related U.S. Application Data

(63) Continuation of application No. 08/231,095, filed on Apr. 22, 1994, now abandoned.

(30) Foreign Application Priority Data

Feb. 22, 1994 (EP) ............................................. 94102622

(51) Int. Cl.⁷ ................................................. C12P 7/52
(52) U.S. Cl. ........................ 435/141; 435/119; 435/170
(58) Field of Search ................................. 435/119, 141, 435/819, 170

(56) References Cited

U.S. PATENT DOCUMENTS 4,794,080 A * 12/1988 Mays ........................ 435/42

OTHER PUBLICATIONS

Menon et al., Arch. Biochem. Biophys. (1967), 121(2), 304–10.*
Stanbury et al., Principles of Fermentation Technology, Pergamon Press, 1984, p. 16–19.*
Rehm et al., "Biotechnology". vol. 2, 1985, VCH, pp. 294–307.*
Kobayachi, T., Bioreactors Biotransformations, 1987, p. 158–165.*
Yougsmith et al., J. Ferment. Technol., vol. 61(6), 1983, p. 593–598.*
G. Belfort, "Fluid Mechanics in Membrane Filtration: Recent Developments," Journal of Membrane Science, vol. 40, pp. 123–147 (1989).

* cited by examiner

*Primary Examiner*—Irene Marx
(74) *Attorney, Agent, or Firm*—Finnegan, Henderson, Farabow, Garrett & Dunner, LLP

(57) ABSTRACT

The present invention relates to a fermentation process which is useful for the simultaneous production of propionic acid and vitamin $B_{12}$, characterized in that it employs the culturing, on a suitable culture medium, of at least one microorganism suitable for the production of vitamin $B_{12}$ and propionic acid, and in that the corresponding fermentation is carried out in continuous fashion and involves at least two successive stages, a first stage associated with the optimal production of propionic acid, and a second with the optimal production of vitamin $B_{12}$.

15 Claims, No Drawings

CONTINUOUS FERMENTATION PROCESS WHICH IS USEFUL FOR THE SIMULTANEOUS OPTIMAL PRODUCTION OF PROPIONIC ACID AND VITAMIN $B_{12}$

This application is a continuation of application Ser. No. 08/231,095, filed Apr. 22, 1994, now abandoned.

FIELD OF THE INVENTION

The present invention relates to a continuous fermentation process which is suitable for the simultaneous and optimized production of vitamin $B_{12}$ and propionic acid.

BACKGROUND OF THE INVENTION

Propionic acid and vitamin $B_{12}$ are two compounds involved in a large number of industrial operations.

As main outlets for propionic acid, there may be mentioned, in particular, the food industry, in which it is employed as a fungicide in the form of calcium and sodium propionates, the cellulose-based plastics industry and the perfumery sector.

Vitamin $B_{12}$, for its part, is an important cofactor in the metabolism of carbohydrates, lipids, amino acids and nucleic acids. Vitamin $B_{12}$ is, moreover, a therapeutic agent used in chemotherapy.

Generally speaking, vitamin $B_{12}$ is prepared by fermentation. The two main corresponding genera of microorganisms employed for its preparation at industrial level are *Propionibacterium* and *Pseudomonas*.

It is noted that, in the standard techniques of production of vitamin $B_{12}$ using microorganisms of the genus *Propionibacterium* the growth of these latter becomes impaired during the fermentation process, leading to a fall in productivity with respect to vitamin $B_{12}$. This is the direct consequence of the concomitant formation of propionic acid in the culture medium. The amount of propionic acid increases during the fermentation process, and reaches a certain limit which inhibits the growth of the said microorganisms.

Traditionally, the industrial production of propionic acid is chiefly carried out by petrochemical methods.

Production by fermentation also proves possible, but is not satisfactory from an industrial standpoint. In general, it employs the assimilation of glucose by *propionibacteria* and leads to the formation of propionic acid but also of not insignificant amounts of acetic acid. Lastly, according to this fermentation process, low yields of propionic acid are obtained on account of the phenomenon already described above in the case of vitamin $B_{12}$ production, namely an inhibition of the growth of the *Propionibacterium* bacteria by propionic acid.

DESCRIPTION OF THE INVENTION

The purpose of the present invention is to propose a production process common to vitamin $B_{12}$ and propionic acid.

This process employs the fermentation of a single stain of microorganism leading, via a single fermentation process, to optimized amounts of propionic acid and vitamin $B_{12}$.

More specifically, the present invention relates to a fermentation process which is useful for the simultaneous production of propionic acid and vitamin $B_{12}$, characterized in that it employs the culturing, on a suitable culture medium, of at least one microorganism suitable for the production of vitamin $B_{12}$ and propionic acid, and in that the corresponding fermentation is carried out in continuous fashion and involves at least two successive stages, a first stage associated with the optimal production of propionic acid, and a second with the optimal production of vitamin $B_{12}$.

Unexpectedly, the claimed process leads, as a result of its two-stage organization and the choice of a strain capable of producing propionic acid and vitamin $B_{12}$ by fermentation and under sufficiently closely related culture conditions, to optimized yields of propionic acid and vitamin $B_{12}$. By its two-stage organization, the claimed process, leads to the recovery, in a first stage of an optimized amount of the extracellularly formed compound, i.e., the propionic acid, and in a second stage of an optimized amount of the intracellularly formed compound, i.e., the vitamin $B_{12}$, whose recovery involves the disruption of the cells.

Moreover, the claimed process is particularly useful, but not limited, for processes involving microorganisms whose growth is inhibited by the propionic acid.

Advantageously, the optimized production of propionic acid obtained according to the invention does not affect the cell growth of the microorganisms, and is hence not detrimental to the subsequent production of vitamin $B_{12}$.

The strain of microorganism employed according to the invention preferably belongs to the genus *Propionibacterium*. It makes no difference whether the strain in question is of the wild-type or otherwise. Many strains of this genus have already been the subject of description in the literature.

A deposit of a microorganism belonging to the genus *Propionibacterium*, and in particular, the *Propionibacterium acidipropionic* strain DSM 8250, has been made in the following IDA depository to comply with the requirements under the Budapest Treaty on the International Recognition of the Deposit of Microorganism for the purpose of Patent Procedure: DEUTSCHE SAMMLUNG, Von Mikrorganismen und Zellkulturen Gmbh (DsM), Mascheroder Weg 1b, D-38124 Branschweig, GERMANY. This deposit material has been accorded the accession number DSM 8250.

The microorganism *Propionibacterium acidipropionici* DSM 8250 is introduced in each of the two stages at a cell concentration of at least 50 g/l, and preferably of the order of 75 g/l, expressed as dry biomass. Naturally, these concentration values are provided only as a guide and do not constitute a limit of the field of the invention. They can, in effect, vary in accordance with the other parameters of the process (fermenter volume, nature of the microorganism, components of the nutrient medium, etc.).

The use of *Propionibacterium acidipropionici* strain DSM 8250 is especially advantageous.

Its use on suitable culture media, that is to say media to which traditional additives and those specific to propionic acid or vitamin $B_{12}$ production are added, leads, under appropriate culture conditions, to very satisfactory yields of propionic acid and vitamin $B_{12}$.

Acetic acid, which is usually formed during traditional processes of fermentation of propionic acid, is obtained in the present case only in small amounts. An acetic acid/propionic acid ratio of less than 0.3, or even of less than 0.2, in anaerobic conditions is obtained in the first stage.

Lastly, as an advantageous and unexpected feature, this strain of microorganism assimilates sucrose as a carbon substrate.

The use of sucrose as a carbon substrate, alone or mixed with at least one other carbon source, within the culture medium, constitutes a preferred embodiment of the claimed process.

The sucrose may be introduced as it is as a carbon source or, more preferably, in the form of molasses. The sucrose concentration in molasses varies according to the nature of the latter. Generally speaking, it varies between approximately 15 and 70% of carbohydrate per kg of molasses.

This feature of the process is advantageous from an economic standpoint.

In effect, molasses is a raw material which is available in large amounts and is consequently inexpensive. To be able to optimize its use in the production of propionic acid and vitamin $B_{12}$ is of great industrial importance in respect of profitability in terms of cost.

The sucrose is preferably employed as a carbon substrate at a concentration varying roughly between 30 and 170 g/l. It is important to note that no inhibition is observed with such concentrations.

Naturally, the culture medium employed for the fermentation contains, besides sucrose, the traditional components, namely at least one assimilable nitrogen source, growth factors, mineral salts required for the growth of the said microorganism and, where appropriate, other carbon substrates.

The assimilable nitrogen source can, for example, originate from proteins extracted from cereals (wheat, maize, etc.), yeasts (extract, cream of yeast), extract of corn steep, malt, peptone, ammonia, ammonium salt and/or casein.

Growth factors, for their part, are traditionally introduced into the culture medium in the form of a yeast or corn steep liquor. The use of molasses as a carbon substrate is also advantageous in this connection. As a result of its composition, it already partly supplies the nutrient medium with these growth factors.

As regards mineral salts, these are, generally speaking, ammonium sulphate, magnesium sulphate, potassium phosphate, cobalt salts, etc.

Since the *Propionibacterium acidipropionici* strain is not capable of producing 5,6-dimethylbenzimidazole (DBI), it is necessary to introduce the latter into the fermentation medium for the formation of 5,6-dimethylbenzimidazolylcobamide. In the case of propionic acid production, it will be introduced at a concentration of the order of 2 mg/l. As regards, more especially, vitamin $B_{12}$ production, this amount will be increased to a value of the order of 10 mg/l.

In the context of the present invention, the nitrogen source can be provided by a yeast extract. Its use at a concentration of the order of 12 g/l proves especially advantageous in relation to the yield of propionic acid and/or vitamin $B_{12}$.

In the particular case of vitamin $B_{12}$ production, betaine can be also added to the culture medium, which is further enriched with cobalt salts.

Traditionally, the fermentation is carried out in the two stages of the claimed process at a pH of the order of 6.5 and a temperature of the order of 37° C. or higher. Naturally, these parameters, together with the oxygenation conditions, are adjusted more precisely in each stage in relation to the product being prepared therein. More particularly, the first stage involves anaerobic conditions while the optimal production of vitamin $B_{12}$, in the following step, needs aerobic condition. The propionic acid and vitamin $B_{12}$ formed are both collected, in continuous or discontinuous fashion, during their respective stages.

Thus, during the first stage, propionic acid production is performed in a first fermenter under anaerobic conditions at a temperature of the order of 37° C. and a pH of approximately 6.5. The fermenter is fed at a dilution rate of the order of 0.25 $h^{-1}$, and the propionic acid formed is collected continuously or discontinuously, from the said fermenter, and the fermentation medium is partly recycled, continuously or sequentially, in the second stage designed for vitamin $B_{12}$ production.

Advantageously, a module permitting cell recycling may be fitted to this first fermenter. A large increase in the cell density ensues. This cell recycling may be performed via an ultrafiltration module, for example. It is naturally within the capacity of a person skilled in the art to fit such a module to the fermenter and to fix the parameters for its use. Under these conditions, the propionic acid formed during the fermentation process in the fermenter of the first stage is isolated cell-free, continuously or discontinuously, from the filtration module.

By way of illustration of the present invention, a fermentation of molasses with *Propionibacterium acidipropionici* strain DSM 8250, under the abovementioned working conditions, with an initial biomass concentration of the order of 75 g/l and a dilution rate of the order of 0.25 $h^{-1}$, leads to an especially impressive hourly productivity per unit volume, since it is of the order of 3 to 5 $g.l^{-1}.h^{-1}$ dependent on using substrate. In addition, the fraction of acetic acid obtained according to the process of the invention proves relatively small. Thus, for the abovementioned working conditions, the acetic acid/propionic acid fraction is less than 0.3 (dependent on using substrate), against 0.45 for the traditional fermentation processes.

Naturally, these values are provided only by way of illustration of the process according to the invention, and do not constitute limits to its field of application.

Vitamin $B_{12}$ optimal production, for its part, is carried out according to the present invention in a second stage, following on from the first, in a second fermenter mounted in series with respect to the first fermenter. The second fermenter is fed during the fermentation process, continuously or sequentially, with fermentation medium originating from the first fermenter.

In order to optimize vitamin $B_{12}$ production therein, the fermentation is carried out under micro-aerobic conditions at a temperature of the order of 40° C. and a pH of approximately 6.5. The culture medium employed for vitamin $B_{12}$ production contains, in addition, sufficient amounts of cobalt salts and dimethylbenzimidazole and optionally of betaine.

The dilution of the fermentation medium of this second fermenter is effected via the first fermenter. Naturally, the corresponding dilution rate is adjusted in accordance with the growth rate developed in the first fermenter, which growth rate is itself dependent on the consumed substrate. It is clear that such adjustments are made on the basis of the fundamental knowledge of a person skilled in the art, and constitute simple routine operations. At the end of the fermentation process, the vitamin $B_{12}$ is extracted according to standard techniques.

According to this embodiment, for a biomass concentration of 75 g/l with the other working parameters as mentioned above, an hourly productivity per unit volume of vitamin $B_{12}$ of the order of 0.4 to 1.5 $mg.l^{-1}h^{-1}$ is obtained dependent on using substrate.

The process which is the subject of the present invention makes it possible advantageously to obtain two compounds which are as different as vitamin $B_{12}$ and propionic acid in satisfactory yields and high concentrations via a continuous culture. It leads, in particular, to a yield of the order of 0.3 to 0.5 g of propionic acid per gram of carbohydrate, without consideration of intercellular produced vitamin in the first stage. Concerning the yield in vitamin $B_{12}$, it is more difficult to evaluate it. We assume that it is of the order of 0.2 to 0.3 mg of vitamin $B_{12}$ per gram of carbohydrate.

EXAMPLES

The examples presented below, without implied limitation of the present invention, will enable further advantages of the claimed process to be demonstrated.

Materials and Analytical Methods

Materials:

Fermentations are carried out in reactors equipped with stirrers and possessing a working volume of 1.5 liter. They are initiated in a discontinuous culture (batch culture) and then, after approximately 30 hours, converted into a continuous culture.

In the case of a cell recycling at the first reactor, a sterilizable ultrafiltration module, equipped with a polysulphone ultraporous capillary column 500 μm in diameter (pore diameter 0.01 μm), is used. During this cell recycling, the contents of the reactor are pumped through the ultrafiltration module at an approximate flow rate of 40 l/h.

A control system is fitted to check the pH, temperature and feed of substrate during the process.

The modifications of cell densities are assessed by the optical density measured using a photometer. The control system takes account of the corresponding data.

The pumps employed for pumping the filtrate cleared of cells to the ultrafiltration module or for pumping the fermentation medium directly to the fermenter are also controlled by the control system, and the cell concentration is adjusted accordingly.

Analytical Methods

Cell concentrations are determined by measuring the optical density at 578 nm.

The amount of dry biomass is evaluated after centrifugation at 10,000 rpm and drying for 24 h at 80° C.

As a carbon substrate, either sugar at a concentration of the order of 50 g/l of sucrose, or blackstrap molasses originating either from beet (45 g/l expressed as sucrose) or from cane sugar (50 g/l expressed as sucrose), or invert molasses originating from cane sugar (31 g/l expressed as carbohydrate), is used. The amounts of sucrose, glucose and fructose are determined by HPLC combined with a refractometer (distilled water was used as mobile phase). Invert molasses possesses approximately 16% of sucrose, 27% of glucose and 25% of fructose per kg. Blackstrap molasses, on the other hand, contains 50 to 45% of sucrose.

The amounts of propionic acid and acetic acid are determined by gas chromatography using a flame ionization detector on a 2-meter column of Chromosorb 101.

At the end of the fermentation, the bacteria are burst in 0.1 M phosphate buffer solution with 0.01% KCN at pH 6 and for 10 minutes at 121° C. The amount of vitamin $B_{12}$ formed intracellularly is evaluated spectrophotometrically in dicyano form at wavelengths of 367 and 580 nm with extinction coefficients of $30.4 \times 10^3$ and $10.2 \times 10^3$, respectively. The isolation of the vitamin $B_{12}$ from the cells as well as its purification may be carried out by various methods commonly practised by a person skilled in the art and which, on that account, will not be recalled here.

In the case of the present invention, the vitamin $B_{12}$ is produced intracellularly in the form of 5,6-dimethylbenzimidazolylcobamide.

Preparation of the Inoculum

*Propionibacterium acidipropionici* strain DSM 8250 is used

The storage medium contains, per liter of deionized water, 1 g of $KH_2PO_4$, 2 g of $(NH_4)_2HPO_4$, 2.5 mg of $FeSO_4.7H_2O$, 10 mg of $MgSO_4.7H_2O$, 2.5 mg of $MnSO_4.H_2O$, 10 mg of NaCl, 10 mg of $CaCl_2.H_2O$, 10 mg of $CoCl_2.6H_2O$, 5.0 g of yeast extract, 1.0 g of sugars and 15 g of agar. The culture is incubated on this medium at 30° C., stored at 4° C. and transferred to a fresh agar medium every month. For the autoclaving operation, the pH is adjusted to a value of between 6.8 and 7.2.

The preculture medium possesses the same concentration as the storage medium. On the other hand, it does not contain agar and its sucrose concentration is increased to a value of 20 g/l.

Example 1

The culture is transferred from the agar medium to an Erienmeyer with 150 ml of culture medium described above and stored at 30° C. After 48 h of storage, 150 ml of the fermentation medium are inoculated with 20 ml of the prepared preculture. The fermenter is inoculated with this preculture at a volume ratio of 15% after 24 hours. The compositions of the culture media employed in each of the stages of the process are described in Table I below.

TABLE I

| COMPOSITION OF THE CULTURE MEDIUM | 1st STAGE PRODUCTION OF PROPIONIC ACID | 2nd STAGE PRODUCTION OF VITAMIN $B_{12}$ |
|---|---|---|
| Yeast extract | 12 g/l | rest. |
| $KH_2PO_4$ | 2 g/l | rest. |
| $MgSO_4.7H_2O$ | 200 mg/l | rest. |
| $FeSO_4.7H_2O$ | 2.5 mg/l | rest. |
| $CoCl_2.6H_2O$ | 20 mg/l | 100 mg/l |
| 5,6-DBI | 2 mg/l | 10 mg/l |
| pH | 6.5 | 6.5 |
| Temperature | 37° C. | 40° C. |
| Oxygenation | anaerobic | micro-aerobic (0.5 vvm at 100 rmp) |

All the substrates and nutrients needed for propionic acid production are introduced into the first fermenter. This first fermentation is carried out in the absence of oxygen at a pH value of 6.5 adjusted, if necessary, with 12% aqueous ammonia solution, and at a temperature of 37° C. The propionic acid contained in the fermentation medium is recovered via an ultrafiltration module.

The process control system makes it possible to maintain a constant cell concentration and a constant working volume within the first fermenter while recovering the propionic acid formed via the filtration module, or alternatively on transferring the fermentation medium with the cells from the first fermentation stage to the second fermentation stage.

The increasing vitamin $B_{12}$ production in the second reactor, is resulted with an aeration of 0.5 vvm at a pH value of 6.5, which is also adjusted, where appropriate, with 6% aqueous ammonia solution, and at a temperature of 40° C.

The productivities with respect to propionic acid and vitamin $B_{12}$ obtained at the end of the fermentation process are presented in Table II below.

TABLE II

|  | BIOMASS | DILUTION | ASSAY | ASSAY g/l | PRODUCTIVITY |
|---|---|---|---|---|---|
| 1st stage | 75 g/l | 0.25 h$^{-1}$ | Propionic acid: 17.7 g/l | Acetic acid 5.0 | Propionic acid 4.2–4.4 g.l$^{-1}$.h$^{-1}$ |
| 2nd stage | 75 g/l | 0.03 h$^{-1}$ | Vitamin B$_{12}$: 49 mg/l | — | Vitamin B$_{12}$: 1–1.5 mg.l$^{-1}$.h$^{-1}$ |

Example 2

Advantages of cell recycling

TABLE III

|  |  | BIOMASS g/l | DILUTION h$^{-1}$ | PROPIONIC ACID (STAGE 1) | | VITAMIN B$_{12}$ (STAGE 2) | |
|---|---|---|---|---|---|---|---|
|  |  |  |  | Concentration g/l | Productivity g.l$^{-1}$h$^{-1}$ | Concentration mg/l | Productivity mg.l$^{-1}$h$^{-1}$ |
| No cell recycling | 1st stage | 7.0 | 0.03 | 21 | 0.63 | 6.0 | 0.18 |
|  | 2nd stage | 7.0 | 0.03 |  |  |  |  |
| With cell recycling | 1st stage | 75 | 0.25 | 17.7 | 4.4 | 49.0 | 1.5 |
|  | 2nd stage | 75 | 0.03 |  |  |  |  |

The results prove the interest of fitting to the first fermenter a module permitting cell recycling.

Example 3

Influence of the nature of the carbon source.

The following fermentations were performed in the two-stage process with the working conditions and parameters identified in Example 1.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

TABLE IV

| NATURE OF THE CARBON SUBSTRATE (75 g/l) | PRODUCTIVITY WITH RESPECT TO PROPIONIC ACID (g.l$^{-1}$.h$^{-1}$) | YIELD OF PROPIONIC ACID (g/g of sucrose) | PRODUCTIVITY WITH RESPECT TO VITAMIN B$_{12}$ (mg.l$^{-1}$.h$^{-1}$) |
|---|---|---|---|
| Cane sugar blackstrap molasses | 4.42 | 0.5 | 1.53 |
| Beet blackstrap molasses | 4.25 | 0.5 | 1.03 |
| Invert molasses | 3.4 | 0.4 | 0.51 |

What is claimed is:

1. A continuous fermentation process for the production of propionic acid and vitamin B$_{12}$, which comprises:
   culturing a strain of *Propionibacterium* for producing propionic acid and vitamin B$_{12}$, wherein said culturing occurs in at least two successive fermentors, said fermentors comprising
   a first fermentor for producing propionic acid comprising a culture medium for producing propionic acid, wherein said strain of *Propionibacterium* is cultured under anaerobic conditions at a temperature of about 37° C. and a pH of about 6.5, and wherein said propionic acid is recovered from said first fermentor, and
   a second successive, continuous fermentor for producing vitamin B$_{12}$ comprising a culture medium for producing vitamin B$_{12}$ and further comprising an amount of said culture medium from said first fermentor sufficient to inoculate said second fermentor, wherein said strain of *Propionibacterium* is cultured, in the presence of propionic acid, under aerobic conditions at a temperature of about 42° C. and a pH of about 6.5 and wherein vitamin B$_{12}$ is recovered from said second fermentor, and
   provided that said culture medium for producing propionic acid and said culture medium for producing vitamin B$_{12}$ further comprise 5,6-dimethylbenzimidazole, when said strain of *Propionibacterium* is *Propionibacterium acidipropionici*.

2. The process according to claim 1, wherein said strain of *Propionibacterium* is *Propionibacterium acidipropionici*.

3. The process according to claim 1, wherein said strain of *Propionibacterium* is *Propionibacterium acidipropionici* DSM 8250.

4. The process according to claim 1, wherein said strain of *Propionibacterium* is present in the first fermentor and/or the second fermentor at an initial cell concentration of at least 50 g/l dry weight.

5. The process according to claim 4, wherein the initial cell concentration is about 75 g/l dry weight.

6. The process according to claim 1, wherein at least one carbon source chosen from sucrose and molasses is present in said culture medium for producing propionic acid and is present in said culture medium for producing vitamin B$_{12}$.

7. The process according to claim 6, wherein said sucrose is present at a concentration ranging from about 30 to 170 g/l.

8. The process according to claim 1, wherein said culture medium for producing propionic acid is introduced into said first fermentor at a dilution rate of about 0.25 $h^{-1}$ during the fermentation process.

9. The process according to claim 1, wherein said strain of *Propionibacterium* is recycled into said first fermentor.

10. The process according to claim 1, wherein said recycling is carried out via an ultrafiltration module and the propionic acid is recovered from said module.

11. The process according to claim 1, wherein said culture medium for producing propionic acid comprises at least one carbohydrate source and said propionic acid is obtained from said first fermentor in a yield ranging from about 0.3 to 0.5 g of propionic acid per gram of carbohydrate.

12. The process according to claim 1, wherein in said first fermentor, acetic acid is produced in an acetic acid/propionic acid ratio of less than 0.3.

13. The process according to claim 1, wherein in said first fermentor, acetic acid is produced in an acetic acid/propionic acid ratio of less than 0.2.

14. The process according to claim 1, wherein sad recovery of propionic acid from said culture medium of the first fermentor comprises recovering extracellular propionic acid.

15. The process according to claim 1, wherein said recovery of vitamin $B_{12}$ comprises recovering intracellular vitamin $B_{12}$.

* * * * *